US00PP30581P3

(12) United States Plant Patent
Heimovaara

(10) Patent No.: US PP30,581 P3
(45) Date of Patent: Jun. 18, 2019

(54) ***ALSTROEMERIA* PLANT NAMED 'ZALSACHABLU'**

(50) Latin Name: *Alstroemeria hybrida*
Varietal Denomination: Zalsachablu

(71) Applicant: Sjoukje Heimovaara, Oegstgeest (NL)

(72) Inventor: Sjoukje Heimovaara, Oegstgeest (NL)

(73) Assignee: Van Zanten Breeding B.V., Rijsenhout (NL)

( * ) Notice: Subject to any disclaimer, the term of this patent is extended or adjusted under 35 U.S.C. 154(b) by 0 days.

(21) Appl. No.: 15/732,755

(22) Filed: Dec. 23, 2017

(65) Prior Publication Data

US 2019/0069461 P1 Feb. 28, 2019

(51) Int. Cl.
*A01H 5/02* (2018.01)
*A01H 6/00* (2018.01)
*A01H 6/56* (2018.01)

(52) U.S. Cl.
USPC ..... Plt./309
CPC ..... *A01H 6/564* (2018.05)

(58) Field of Classification Search
USPC ..... Plt./309
CPC ..... A01H 5/02; A01H 5/0211; A01H 5/00; A01H 6/564
See application file for complete search history.

(56) References Cited

PUBLICATIONS

New Plants and Flowers, Award sinning fresh flowers at Proflora 2017 Columbia 2017, retrieved on Nov. 8, 2018, retrieved from the Internet at http://www.newplantsandflowers.com/award-winning-fresh-flowers-at-proflora-2017-colombia/, 2 pp. (Year: 2017).*

Royal Van Zanten, Charmelia Blush 2018, retrieved on Nov. 8, 2018, retrieved from the Internet at https://www.royalvanzanten.com/en/products/cut-flowers/charmelia-blush/, one page. (Year: 2018).*

* cited by examiner

*Primary Examiner* — June Hwu
(74) *Attorney, Agent, or Firm* — C. A. Whealy

(57) ABSTRACT

A new and distinct cultivar of *Alstroemeria* plant named 'Zalsachablu', characterized by its erect and moderately strong flowering stems; moderately vigorous growth habit; upright inflorescences with relatively small white to light green and light red-colored flowers without stripes; excellent postproduction longevity; and relative tolerance to high temperatures.

2 Drawing Sheets

Botanical designation: *Alstroemeria hybrida.*
Cultivar denomination: 'ZALSACHABLU'.

BACKGROUND OF THE INVENTION

The present invention relates to a new and distinct cultivar of *Alstroemeria* plant, botanically known as *Alstroemeria hybrida,* commercially used as a cut flower *Alstroemeria,* and hereinafter referred to by the name 'Zalsachablu'.

The new *Alstroemeria* plant is a product of a planned breeding program conducted by the Inventor in Rijsenhout, The Netherlands. The objective of the breeding program is to create new cut flower *Alstroemeria* plants with desirable flower and plant qualities, attractive and unique flower coloration and excellent postproduction longevity.

The new *Alstroemeria* plant originated from a cross-pollination made by the Inventor in Rijsenhout, The Netherlands in May, 2011 of a proprietary *Alstroemeria hybrida* selection identified as code number 9142-5, not patented, as the female, or seed, parent with a proprietary *Alstroemeria hybrida* selection identified as code number 7469-1, not patented, as the male, or pollen, parent. The new *Alstroemeria* plant was discovered and selected by the Inventor as a single flowering plant from within the progeny of the stated cross-pollination in a controlled greenhouse environment in Rijsenhout, The Netherlands in June, 2012.

Asexual reproduction of the new *Alstroemeria* plant by rhizome divisions in a controlled greenhouse environment in Rijsenhout, The Netherlands since September, 2012 has shown that the unique features of this new *Alstroemeria* plant are stable and reproduced true to type in successive generations.

SUMMARY OF THE INVENTION

Plants of the new *Alstroemeria* have not been observed under all possible combinations of environmental conditions and cultural practices. The phenotype may vary somewhat with variations in environmental conditions such as temperature and light intensity without, however, any variance in genotype. The following traits have been repeatedly observed and are determined to be the unique characteristics of 'Zalsachablu'. These characteristics in combination distinguish 'Zalsachablu' as a new and distinct *Alstroemeria* plant:

1. Erect and moderately strong flowering stems.
2. Moderately vigorous growth habit.
3. Upright inflorescences with relatively small white to light green and light red-colored flowers without stripes.
4. Excellent postproduction longevity.
5. Relatively tolerant to high temperatures.

Plants of the new *Alstroemeria* can be compared to plants of the female parent selection. Plants of the new *Alstroemeria* differ from plants of the female parent selection primarily in flower size and color as plants of the female parent selection have larger pink-colored flowers. In addition, flowers of plants of the new *Alstroemeria* do not have developed reproductive organs whereas flowers of plants of the female parent selection have fully-developed stamens and pistils.

Plants of the new *Alstroemeria* can be compared to plants of the male parent selection. Plants of the new *Alstroemeria* differ from plants of the male parent selection primarily in flower size and color as plants of the male parent selection have larger yellow-colored flowers. In addition, flowers of plants of the new *Alstroemeria* do not have developed reproductive organs whereas flowers of plants of the male parent selection have fully-developed stamens and pistils.

Plants of the new *Alstroemeria* can be compared to plants of *Alstroemeria hybrida* 'Zalsabri', disclosed in U.S. Plant Pat. No. 25,213. In side-by-side comparisons, plants of the new *Alstroemeria* differ primarily from plants of 'Zalsabri' in the following characteristics:

1. Flowers of plants of the new *Alstroemeria* and 'Zalsabri' differ in flower color as plants of 'Zalsabri' have pink-colored flowers.
2. Flowers of plants of the new *Alstroemeria* do not have stripes whereas flowers of plants of 'Zalsabri' have stripes.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet is a side perspective view of a typical flowering plant of 'Zalsachablu'.

The photograph on the second sheet is a close-up view of a typical flower of 'Zalsachablu'.

DETAILED BOTANICAL DESCRIPTION

The aforementioned photographs and following observations and measurements describe plants of the new *Alstroemeria* grown during the spring in ground beds in a glass-covered greenhouse in Rijsenhout, The Netherlands. During the production of the plants, day temperatures ranged from 15° C. to 25° C., night temperatures ranged from 10° C. to 15° C., soil temperatures averaged 14° C. and light levels averaged 5,000 lux. Plants were three months old when the photographs and description were taken. In the following description, color references are made to The Royal Horticultural Society Colour Chart, 2015 Edition, except where general terms of ordinary dictionary significance are used.

Botanical classification: *Alstroemeria hybrida 'Zalsachablu'*.

Parentage:

*Female, or seed, parent*.—Proprietary *Alstroemeria hybrida* selection identified as code number 9142-5, not patented.

*Male, or pollen, parent*.—Proprietary *Alstroemeria hybrida* selection identified as code number 7469-1, not patented.

Propagation:

*Type*.—In vitro rhizogenesis.

*Time to produce a rooted young plant, summer*.—About 40 days at temperatures of 16° C. to 25° C.

*Time to produce a rooted young plant, winter*.—About 60 days at temperatures of 16° C. to 20° C.

*Root description*.—Fibrous, fleshy, thick; color, close to 155D.

*Rooting habit*.—Freely branching; medium density.

*Rhizomes*.—Shape: Elongate; rounded. Length: About 10 cm to 30 cm. Diameter: About 3 mm to 10 mm. Texture: Smooth. Color: Close to 155D.

Plant description:

*Plant and growth habit*.—Upright; freely basal branching, bushy appearance; moderately vigorous growth habit; rapid growth rate.

*Plant height*.—About 145 cm to 155 cm.

*Plant diameter (spread)*.—About 14 cm to 18 cm.

Flowering stem description:

*Aspect*.—Erect to about 10° from vertical.

*Length*.—About 145 cm to 155 cm.

*Internode length*.—About 1 cm to 4 cm.

*Strength*.—Moderately strong.

*Texture and luster*.—Smooth, glabrous; semi-glossy.

*Color, developed and fully developed*.—Close to 138B.

Leaf description:

*Arrangement*.—Alternate, simple.

*Length*.—About 16 cm to 20 cm.

*Width*.—About 3.5 cm to 4.5 cm.

*Shape*.—Elliptical.

*Apex*.—Acute.

*Base*.—Cuneate.

*Margin*.—Entire.

*Texture and luster, upper surface*.—Smooth, glabrous; semi-glossy.

*Texture and luster, lower surface*.—Ribbed, glabrous; matte.

*Aspect*.—Upright to somewhat horizontal, twisting.

*Venation pattern*.—Parallel.

*Color*.—Developing and fully developed leaves, upper surface: Close to NN137A; venation, close to 143C. Developing and fully developed leaves, lower surface: Close to N138A; venation, close to 143A.

*Petioles*.—Length: About 2 cm to 3 cm. Diameter: About 5 mm to 7 mm. Texture and luster: Smooth, glabrous; matte. Strength: Low, flexible. Color, upper surface: Close to 143C. Color, lower surface: Close to N138A.

Flower description:

*Flower type and habit*.—Single cup-shaped flowers arranged in umbels; flowers face mostly upright; perianth segments separate; freely flowering habit, about 35 flower buds and open flowers per plant at one time; typically, about 15 flowers developing per inflorescence.

*Natural flowering season*.—Flowering continuous from the spring until the autumn in The Netherlands; plants begin flowering about 80 to 90 days after planting.

*Fragrance*.—None detected.

*Flower longevity*.—About two to four weeks on the plant and about three weeks as a cut flower; flowers persistent.

*Flower buds*.—Length: About 3 cm. Diameter: About 1.5 cm. Shape: Roughly ovoid. Texture and luster: Smooth, glabrous; semi-glossy. Color: Close to 155A and 143A.

*Umbel height*.—About 22 cm.

*Umbel diameter*.—About 16 cm.

*Flower diameter*.—About 3 cm.

*Flower height*.—About 3 cm to 5 cm.

*Flower depth*.—About 4 cm.

*Perianth*.—Arrangement: Six arranged in two whorls, each whorl with two lateral and one median segments. Inner perianth, lateral segments: Length: About 3.5 cm. Width: About 7 mm. Shape: Elliptical. Apex: Cuspidate. Base: Attenuate. Margin: Proximally, entire and distally, finely dentate. Texture, upper surface: Smooth, glabrous; semi-glossy. Texture, lower surface: Ribbed, glabrous; matte. Color, when opening and fully opened, upper surface: Proximally, close to 155A and distally, close to 60B; towards the base and venation, close to N144C and N144D; colors do not fade with development. Color, when opening and fully opened, lower surface: Proximally, close to 155A and distally, close to 60B; apex, close to 141B; venation, proximally, close to 155A and distally, close to 60B; colors do not fade with development. Inner perianth, median segment: Length: About 3.5 cm. Width: About 7 mm. Shape: Elliptical. Apex: Cuspidate. Base: Attenuate. Margin: Proximally, entire; distally, finely dentate. Texture, upper surface: Smooth, glabrous; semi-glossy. Texture, lower surface: Ribbed, glabrous; matte. Color, when opening and fully opened, upper surface: Proximally, close to 155A and distally, close to between 60B and 62B; apex, close to 141B; towards the base and venation, close to N144C and N144D; colors do not fade with development. Color, when opening and fully opened, lower surface: Proximally, close to 155A and distally, close to between 60B and 62B; apex and venation, close to 51B; colors do not fade with development. Outer perianth, lateral segments: Length: About 3.9 cm. Width: About 2.1 cm. Shape: Obovate. Apex: Wishbone-shaped; medium in depth. Base: Attenuate. Margin: Entire. Texture, upper surface: Ribbed, glabrous; semi-glossy. Texture, lower surface: Ribbed, glabrous; matte. Color, when opening and fully opened, upper surface: Proximally, close to 155A and distally, close to between 60B and 62B; towards the base, close to N144C and N144D; apex and venation, close to 141B; colors do not fade with development. Color, when opening and fully opened, lower surface: Proximally, close to 155A and distally, close to 60B; apex and venation, close to 141A; colors do not fade with development. Outer perianth, median segment: Length: About 3.9 cm. Width: About 2.1 cm. Shape: Obovate. Apex: Wishbone-shaped; medium in depth. Base: Attenuate. Margin: Entire. Texture, upper surface: Ribbed, glabrous; semi-glossy. Texture, lower surface: Ribbed, glabrous; matte. Color, when opening and fully opened, upper surface: Proximally, close to 155A and distally, close to 60B; towards the base, close to N144C and N144D; apex and venation, close to 141B; colors do not fade with development. Color, when opening and fully opened, lower surface: Proximally, close to 155A and distally, close to 60B; apex and venation, close to 141A; colors do not fade with development.

*Pedicels*.—Length: About 6 cm to 8 cm. Diameter: About 2.5 mm. Strength: Moderately strong. Angle: About 30° from vertical. Texture and luster: Smooth, glabrous; matte. Color, upper and lower surfaces: Close to 138A to 138B.

*Reproductive structures*.—Reproductive structures have not been observed to develop on plants of the new *Alstroemeria* to date.

*Seeds and fruits*.—Seed and fruit development has not been observed on plants of the new *Alstroemeria* to date.

Disease & pest resistance: Plants of the new *Alstroemeria* have not been observed to be resistant to pathogens and pests common to *Alstroemeria* plants to date.

Temperature tolerance: Plants of the new *Alstroemeria* have been observed to tolerate temperatures from about −5° C. to about 40° C.

It is claimed:

1. A new and distinct *Alstroemeria* plant named 'Zalsachablu' as illustrated and described.

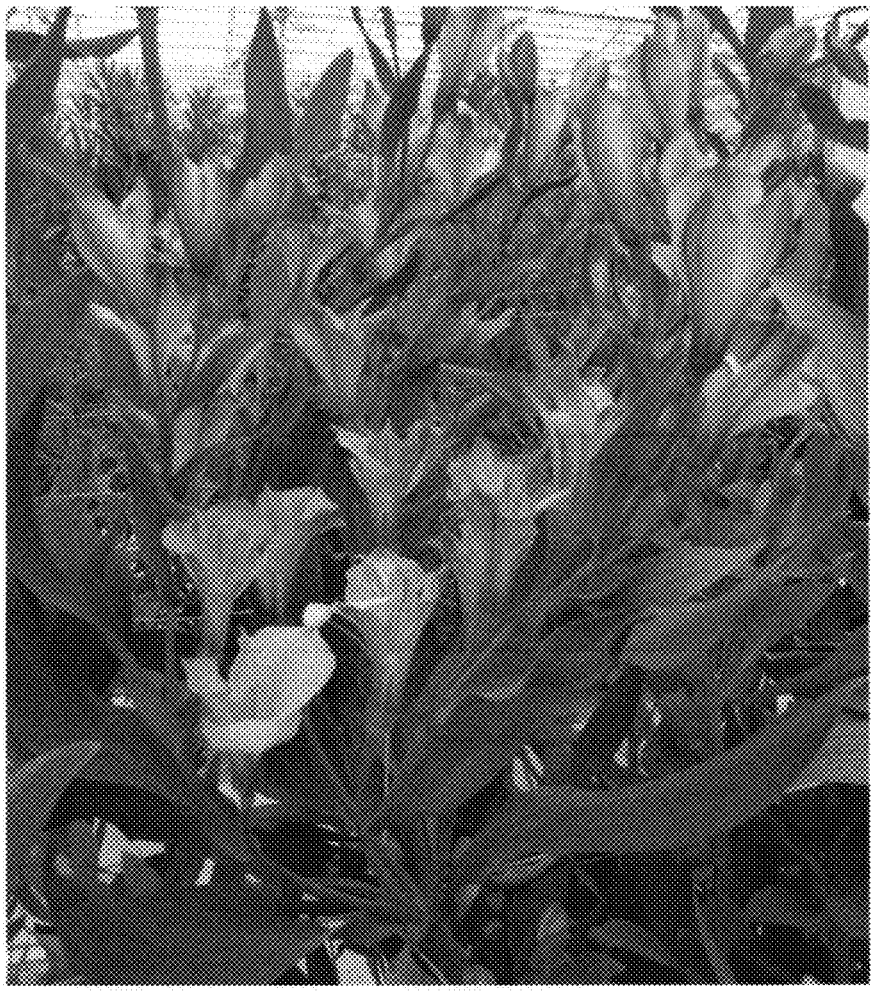

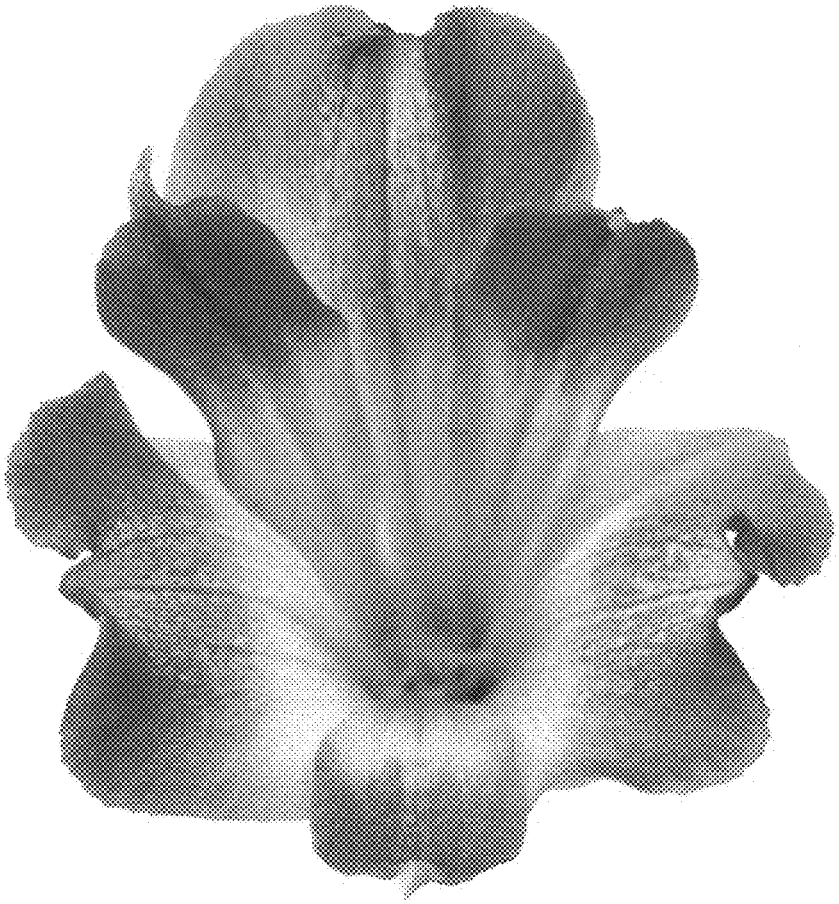

* * * * *